(12) United States Patent
Mitsutake et al.

(10) Patent No.: US 9,636,849 B2
(45) Date of Patent: May 2, 2017

(54) MOLD RELEASE AGENT FOR WATER GLASS-CONTAINING SAND MOLD MOLDING

(71) Applicants: TOYOTA JIDOSHA KABUSHIKI KAISHA, Toyota-shi, Aichi (JP); TETRA CO., LTD., Kasugai-shi, Aichi (JP)

(72) Inventors: Masaomi Mitsutake, Toyota (JP); Hirotsune Watanabe, Toyota (JP); Masaki Okada, Toyota (JP); Hiroyuki Matsubara, Kasugai (JP)

(73) Assignees: TOYOTA JIDOSHA KABUSHIKI KAISHA, Toyota-shi, Aichi-ken (JP); TETRA CO., LTD, Kasugai-shi, Aichi-ken (JP)

( * ) Notice: Subject to any disclaimer, the term of this patent is extended or adjusted under 35 U.S.C. 154(b) by 0 days.

(21) Appl. No.: 14/767,748

(22) PCT Filed: Oct. 24, 2014

(86) PCT No.: PCT/JP2014/078378
§ 371 (c)(1),
(2) Date: Aug. 13, 2015

(87) PCT Pub. No.: WO2015/064506
PCT Pub. Date: May 7, 2015

(65) Prior Publication Data
US 2016/0236267 A1    Aug. 18, 2016

(30) Foreign Application Priority Data

Oct. 28, 2013    (JP) ................................ 2013-223678

(51) Int. Cl.
*B29C 33/60*    (2006.01)
*B22C 3/00*    (2006.01)
(Continued)

(52) U.S. Cl.
CPC ............... *B29C 33/60* (2013.01); *B22C 3/00* (2013.01); *C07C 55/02* (2013.01); *C08G 77/04* (2013.01);
(Continued)

(58) Field of Classification Search
None
See application file for complete search history.

(56) References Cited

U.S. PATENT DOCUMENTS 2,272,847 A * 2/1942 Macht .................... B29C 33/60
106/38.22
2,770,859 A * 11/1956 Henry ..................... B22C 23/00
106/38.25
2014/0284015 A1* 9/2014 Mitsutake ................ B22C 7/06
164/37

FOREIGN PATENT DOCUMENTS

JP    4726933 B    7/1972
JP    57-146468    *    9/1982    ............. B22D 27/18
(Continued)

OTHER PUBLICATIONS

JP59-001497 (JP57-146468), Wada, et al., Mold Containing Material for Casting Steel Ingot, 1982.*
(Continued)

*Primary Examiner* — Yate K Cutliff
(74) *Attorney, Agent, or Firm* — Sughrue Mion, PLLC

(57) ABSTRACT

[Task] There is provided a mold release agent for forming a water glass-containing sand mold with high release properties which can prevent attachment of a water glass to a flask and the accumulation of the water glass on the flask in the formation of the sand mold when using the water glass as a binder.
[Solution] The mold release agent for forming the water glass-containing sand mold is structured to contain an organic compound, the organic compound having a proton-
(Continued)

$$Na_2O \cdot nSiO_2 \cdot xH_2O + 2R-H \rightarrow nSiO_2 + (x+1)H_2O + 2R-Na$$

Water glass    Proton-donating    Silicon dioxide    Water    Organic salt
Functional group High adhesive properties | No adhesive properties donating functional group that reacts with the water glass to produce silicon dioxide. The water glass contained in a raw material for the sand mold reacts with the proton-donating functional group contained in the mold release agent so as to produce silicon dioxide. Since silicon dioxide has no adhesion, it can prevent that the attachment (fixing) of the water glass contained in a formed sand mold to the flask and the accumulation of the water glass on the flask.

3 Claims, 1 Drawing Sheet

(51) Int. Cl.
C07C 55/02 (2006.01)
C08G 77/04 (2006.01)
B22C 1/00 (2006.01)
B22C 9/02 (2006.01)
B22C 1/18 (2006.01)

(52) U.S. Cl.
CPC ............... *B22C 1/00* (2013.01); *B22C 1/188* (2013.01); *B22C 9/02* (2013.01)

(56) References Cited

FOREIGN PATENT DOCUMENTS

| JP | 9-174194 A | 7/1997 |
| JP | 2013111602 A | 6/2013 |
| JP | 2013166176 A | 8/2013 |

OTHER PUBLICATIONS

Koonce, S.D., et al., A Historical Review of the Chemistry of Carnauba Wax, 1944, Oil & Soap (JAOCS) vol. 21, issue 6, pp. 167-170.*
Van Nostrand's Scientific Encyclopedia, Release Agents, 2006 John Wiley & Sons, inc. pp. 1-10.*
Communication dated Jul. 6, 2016 issued by the Japanese Patent Office in counterpart application No. 2015544974.

* cited by examiner

Water glass — Proton-donating Functional group — Silicon dioxide — Water — Organic salt

| High adhesive properties | | No adhesive properties |

(A typical chain structure includes a carbon chain (—CCCCC—), a siloxane chain (—OSi OSi O—), etc.)

Water glass — Carboxyl group — Silicon dioxide — Water — Organic salt

| High adhesive properties | | No adhesive properties |

MOLD RELEASE AGENT FOR WATER GLASS-CONTAINING SAND MOLD MOLDING

TECHNICAL FIELD

The present invention relates to a mold release agent used in forming a sand mold using water glass as a binder (mold release agent for forming a water glass-containing sand mold).

BACKGROUND ART

Conventionally, a technique of forming a casting mold using foundry sand to which water glass is added was used (Patent Document 1). This technique is a technique in which 1 to 4% (% by weight) of water glass is added and kneaded in foundry sand, and a casting mold is formed from the kneaded mixture, and then dried.

PRIOR ART DOCUMENTS

Patent Document

Patent Document 1: Japanese Patent Application Publication No. H9-174194 (JP H9-174194 A)

SUMMARY OF THE INVENTION

Problem to Be Solved By the Invention

When a sand mold (casting mold: main mold and core) is formed using water glass as a binder as in BACKGROUND ART described above, water glass (sodium silicate) is easily attached (fixed) to a flask used in forming the sand mold, and the sand mold is likely to collapse during mold release. This is because water glass has high affinity to another substance such as metal.

Water glass is likely to accumulate on the flask, even though the sand mold can be released. The flask has an aperture for removing air while filling the flask with sand containing water glass and removing steam while baking on the matching surface of the flask. However, the aperture is filled with water glass that has accumulated on the flask, as described above, which prevents removal of air. As a result, the flask may not be sufficiently filled with sand containing water glass, and the sand may not be sufficiently baked. Consequently, development of a high-performance mold release agent (having high release properties) capable of preventing attachment of water glass to the flask and accumulation of water glass on the flask has been demanded.

The present invention is made in view of this demand. It is an object of the present invention to provide a high-performance mold release agent for forming a water glass-containing sand mold which can prevent attachment (fixing) of water glass to a flask and accumulation of water glass on the flask while forming the sand mold (main mold and core) using water glass as a binder.

Means for Solving the Problem

The object can be achieved by a configuration of a mold release agent for forming a water glass-containing sand mold in each aspect described below.

Each aspect is described so as to be divided into a section, in which a number is applied to each section, and a number of another section is quoted as necessary, as in claims. This is only for ease of understanding the present invention, and technical characteristics described here and a combination thereof are not to be interpreted as being limited to the description in the following sections. When a plurality of items is described in one section, the items are not always used together, and only one part of the items may be selected and used.

In the following sections, (1), (2), and (3) correspond to claims 1, 2, and 3, respectively.

(1) A mold release agent for forming a water glass-containing sand mold characterized by comprising an organic compound having a proton-donating functional group that reacts with water glass to produce silicon dioxide.

(2) The mold release agent for forming a water glass-containing sand mold according to (1), characterized in that the proton-donating functional group is a carboxyl group.

(3) A mold release agent for forming a water glass-containing sand mold characterized by comprising a chain organic compound having a proton-donating functional group in an amount of more than 0.0001 mol/kg and 0.0500 mol/kg or less.

Effects of the Invention

The present invention can provide a high-performance mold release agent for forming a water glass-containing sand mold which can prevent attachment (fixing) of water glass to a flask and accumulation of water glass on the flask while forming the sand mold using water glass as a binder.

MODES FOR CARRYING OUT THE INVENTION

Hereinafter, embodiments of the present invention will be described with reference to the drawings.

As described in Problem to be Solved by the Invention, water glass is easily attached (fixed) to a flask due to its high affinity to another substance such as metal. In a case of a method for forming a casting mold through injection filling, a water-containing kneaded mixture (kneaded mixture obtained by adding water glass to foundry sand) is heated to evaporate water content, and then cured by causing a polymerization reaction of water glass. At that time, a pressure is kept being applied by an injection cylinder until the water content is gone, and as a result, an internal pressure due to steam is suppressed to prevent reflux of the kneaded mixture. Consequently, a pressure needs to be applied until the kneaded mixture is cured to prevent reflux. At that time, the kneaded mixture is pressed onto the surface of the flask, water glass is attached (fixed) to the flask, and the kneaded mixture may be extruded from the aperture of the flask. Thus, water glass is likely to accumulate on the flask. Accordingly, a high-performance mold release agent that prevents attachment and accumulation of water glass is necessary.

The present inventors have intensively investigated and performed experiments to solve the problems, and as a result, invented a mold release agent containing an organic compound (e.g., fatty acid) having a proton-donating functional group that reacts with water glass to produce silicon dioxide for formation of a water glass-containing sand mold.

Figure 1:
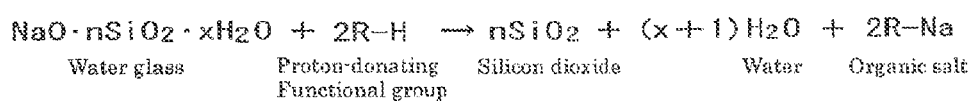
FIG. 1 is a view showing a chemical reaction of a mold release agent for forming a water glass-containing sand mold according to an embodiment of the present invention.

When a substance having a proton-donating functional group that reacts with water glass to produce silicon dioxide, as shown in FIG. 1, is used for formation of a sand mold using water glass as a binder, water glass contained in a raw material for the sand mold reacts with the proton-donating functional group contained in a mold release agent to produce silicon dioxide. Since silicon dioxide has no adhesion, it can prevent attachment (fixing) of water glass contained in a sand mold formed to a flask and accumulation of water glass on the flask.

Specifically, water glass contained in the kneaded mixture is heated to evaporate water content, resulting in a condensation reaction. This causes water glass to form a strong structure in which a bond of O—Si—O forms a three-dimensional net. This structure expresses strength of a casting mold. Before formation of the three-dimensional structure, the substance having a proton-donating functional group in the mold release agent reacts with water glass as an alkali, to produce silicon dioxide. Silicon dioxide is produced on the interface between the casting mold and the flask so as to be able to prevent formation of a three-dimensional net structure between the casting mold and the flask and eliminate adhesion. Further, due to its low-density crystalline structure, pressure contact is prevented, resulting in excellent release properties. Thus, a high-performance mold release agent can be obtained in which attachment and accumulation of water glass can be prevented.

Figure 2:
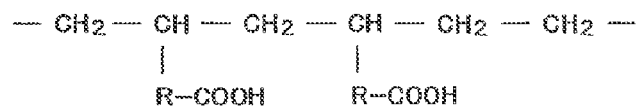
FIG. 2 is a view showing a structure and a chemical reaction of a mold release agent for forming a water glass-containing sand mold according to another embodiment.
Figure 2:
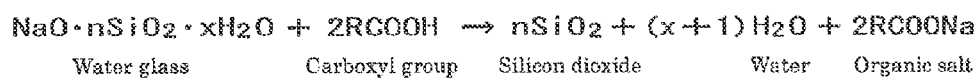

The present invention can particularly provide a high-performance mold release agent that exhibits high release properties when using an organic compound having a carboxyl group as the functional group (FIG. 2 is a representative example of a structural formula thereof and a chemical reaction formula) as described in Experimental Examples below, and prevents attachment and accumulation of water glass.

EXAMPLES

Experimental Example 1

To obtain a high-performance mold release agent for forming a water glass-containing sand mold, an example of the experiment conducted to find an organic compound having a proton-donating functional group is shown below.

Experimental Method

A mold release agent for forming a water glass-containing sand mold (sample) produced from each of 11 different organic chemicals, including materials having different proton-donating functional groups, was used in a test of forming a sand mold through the following procedures. An attached substance to a flask for forming a sand mold was observed.
Procedure 1
A cylindrical flask (cylindrical flask for forming a sand mold) was prepared. An upper flask and a lower flask (collectively referred to as a columnar flask) having a columnar shape, which can be inserted in the cylindrical flask by rubbing and are made of copper alloy, were also prepared. The cylindrical flask, the upper flask, and the lower flask were heated at a predetermined temperature, which was 260° C. here. The sample (mold release agent) was applied to the surfaces of the upper flask and the lower flask coming into contact with a formed object described below and the inner surface of the cylindrical flask with a pressure spray.
Procedure 2
Immediately after the application, the lower flask was inserted in the cylindrical flask, and a raw material for a sand mold (kneaded mixture obtained by adding water glass to foundry sand) was then added.
Procedure 3
The upper flask was inserted in the cylindrical flask from the top thereof, and the raw material for a sand mold was disposed between the upper flask and the lower flask.
Procedure 4
Immediately after the raw material was disposed between the flasks, the upper flask in the cylindrical flask was pressurized in a direction from the top to the bottom.
Procedure 5
After a predetermined period of time, which was one minute later here, the lower flask in the cylindrical flask was pulled out of the cylindrical flask from the bottom.
Procedure 6
Subsequently, the cylindrical flask was reversed (reversely turned), and the upper flask in the cylindrical flask was pulled out of the reversed cylindrical flask from the bottom.
Procedure 7
Then, a formed object remaining in the cylindrical flask (formed object obtained as a sand mold by heating and pressurizing the raw material for a sand mold) was then pressed downward by inserting an extrusion bar into the reversed cylindrical flask from the top, and pulled out of the cylindrical flask.
Procedure 8
The procedures 1 to 7 were repeated five times, to obtain five formed objects. Then, it was observed whether or not an attached substance to the flasks (the cylindrical flask and the columnar flask) was present when the formed object was obtained each time.

Experimental Results

The following observation results are obtained in the experiments.

a) In a case of a chain organic compound (fatty acid) having a proton-donating carboxyl group Water glass is attached to the side of the columnar flask.

The material for the formed object is not attached to the contact surface of the columnar flask with the formed object.

Water glass is not attached to the inner surface of the cylindrical flask.

Carbide does not accumulate on the flask.

b) In a case of a chain organic compound (polysiloxane) having a proton-donating carboxyl group Water glass is attached to the side of the columnar flask.

A white powder that has been produced by a reaction with the carboxyl group is on the contact surface of the columnar flask with the formed object. The white powder can be easily removed by air and is not fixed on the contact surface.

Water glass is not attached to the inner surface of the cylindrical flask.

Carbide does not accumulate on the flask.

c) In a case of a chain organic compound (polysiloxane) having a proton-donating carbonyl group Water glass is attached to the side of the columnar flask.

The material for the formed object is not attached to the contact surface of the columnar flask with the formed object.

Water glass is not attached to the inner surface of the cylindrical flask.

Carbide does not accumulate on the flask.

d) In a case of a chain organic compound (polysiloxane) having a proton-donating hydroxyl group Water glass is not attached to the side of the columnar flask.

The material for the formed object is not attached to the contact surface of the columnar flask with the formed object.

Water glass is not attached to the inner surface of the cylindrical flask.

Carbide does not accumulate on the flask.

e) In a case of only water

Sand in the material for the formed object is attached to the side of the columnar flask.

Sand in the material for the formed object is attached to the contact surface of the columnar flask with the formed object.

Water glass is attached to the inner surface of the cylindrical flask.

Carbide does not accumulate on the flask.

f) In a case of a chain organic compound A (polysiloxane) having no proton-donating functional group Water glass is not attached to the side of the columnar flask.

Sand in the material for the formed object is attached to the contact surface of the columnar flask with the formed object.

Water glass is attached to the inner surface of the cylindrical flask.

Carbide does not accumulate on the flask.

g) In a case of a chain organic compound B (polysiloxane) having no proton-donating functional group Water glass is attached to the side of the columnar flask.

Sand in the material for the formed object is attached to the contact surface of the columnar flask with the formed object.

Water glass is attached to the inner surface of the cylindrical flask.

Carbide does not accumulate on the flask.

h) In a case of a cyclic organic compound (base oil: alkyl naphthalene) having no proton-donating functional group Water glass is not attached to the side of the columnar flask.

Sand in the material for the formed object is attached to the contact surface of the columnar flask with the formed object.

Water glass is not attached to the inner surface of the cylindrical flask.

Carbide does not accumulate on the flask.

i) In a case of a chain organic compound (base oil: poly-α-olefin) having no proton-donating functional group Water glass is not attached to the side of the columnar flask.

The material for the formed object is not attached to the contact surface of the columnar flask with the formed object.

Water glass is attached to the inner surface of the cylindrical flask. Carbide accumulates on the flask.

j) In a case of a cyclic organic compound (base oil: naphthene-based oil) having no proton-donating functional group Water glass is attached to the side of the columnar flask.

The material for the formed object is attached to the contact surface of the columnar flask with the formed object.

Water glass is attached to the inner surface of the cylindrical flask.

Carbide accumulates on the flask.

k) In a case of a polyester organic compound (polyester) having no proton-donating functional group Water glass is attached to the side of the columnar flask.

The material for the formed object is not attached to the contact surface of the columnar flask with the formed object.

Water glass is attached to the inner surface of the cylindrical flask.

Carbide accumulates on the flask.

The experimental results are summarized in Table 1.

TABLE 1

| | | | | | Evaluation | | |
|---|---|---|---|---|---|---|---|
| | | | Material type | | Fixing to contact surface | Fixing to interior | Accumu- |
| Example/ Comparative Example | Material No. | Proton- donating ability | Functional group | Classifi- cation | of columnar flask with formed object | surface of cylindrical flask | lation in flask (carbide) |
| Example | Material 1 | Yes | Carboxyl group | Fatty acid | None | None | None |
| Example | Material 2 | Yes | Carboxyl group | Polysiloxane | Powder (can be removed) | None | None |
| Example | Material 3 | Yes | Carbonyl group | Polysiloxane | None | None | None |
| Example | Material 4 | Yes | Hydroxyl group | Polysiloxane | None | None | None |
| Comparative Example | Material 5 | No | — | Water | Attached (sand) * | Attached (water glass) | None |
| Comparative Example | Material 6 | No | Methyl group | Polysiloxane | Attached (sand) * | Attached (water glass) | None |
| Comparative Example | Material 7 | No | Alkyl/ aralkyl group | Polysiloxane | Attached (sand) * | Attached (water glass) | None |
| Comparative Example | Material 8 | No | — | Lubricating oil (cyclic) | Attached (sand) * | None | None |
| Comparative | Material | No | — | Lubricating | None | Attached (water | Present * |

TABLE 1-continued

| | | Material type | | | Evaluation | | |
|---|---|---|---|---|---|---|---|
| Example/ Comparative Example | Material No. | Proton- donating ability | Functional group | Classifi- cation | Fixing to con- tact surface of columnar flask with formed object | Fixing to interior surface of cylindrical flask | Accumu- lation in flask (carbide) |
| Example | 9 | | | oil (chain) | | glass) | |
| Comparative Example | Material 10 | No | — | Lubricating oil (cyclic) | Attached (sand) * | Attached (water glass) | Present * |
| Comparative Example | Material 11 | No | — | Lubricating oil (ester) | None | Attached (water glass) | Present * |

* represents that the material has a problem

The amount of carboxyl group in Material 1 during the experiment is 0.0500 mol/kg.

The amount of carboxyl group in Material 2 during the experiment is 0.0250 mol/kg.

The amount of functional group in Material 3 during the experiment is 0.0450 mol/kg.

The amount of functional group in Material 4 during the experiment is 0.0550 mol/kg.

Based on the experimental results, the following evaluation results are obtained.

I) For the materials of the samples having a proton-donating functional group, the material for the formed object is not attached (fixed) to the forming surface of the flask.

II) For the materials of the samples having no proton-donating properties, some materials for the formed object are not attached (fixed) to the forming surface of the flask, but water glass is attached to the cylindrical flask, and a carbonated organic substance accumulates on the flask. Therefore, the materials of the samples are not suitable for continuous use as a material for a mold release agent.

III) Based on I) and II), a result is obtained in which the organic compound having a proton-donating functional group can be provided as a mold release agent for forming a water glass-containing sand mold that can solve the problem described above.

Experimental Example 2

To obtain a high-performance mold release agent for forming a water glass-containing sand mold containing an organic compound having a carboxyl group as a proton-donating functional group, an example of the experiment conducted to find a suitable amount of carboxyl group is shown below.

Experimental Method

A mold release agent for forming a water glass-containing sand mold (sample) produced from each of 6 different amounts of carboxyl group (mole amount per unit weight of mold release agent) was used in a test of forming a sand mold through the same procedures as in Experimental Example 1. An attached substance to a flask for forming a sand mold was observed.

Experimental Results

The following observation results are obtained in the experiments.

a) In a case where the amount of carboxyl group (mole amount of carboxyl group per unit weight of the mold release agent, the same applies hereinafter) is 0.1500 mol/kg A large amount of component containing a carboxyl group accumulates due to the organic chain.

A white substance that has been produced by a reaction with the carboxyl group is attached to the formed object.

b) In a case where the amount of carboxyl group is 0.1000 mol/kg

A large amount of component containing a carboxyl group accumulates due to the organic chain.

A white substance that has been produced by a reaction with the carboxyl group is attached to the formed object.

c) In a case where the amount of carboxyl group is 0.0500 mol/kg

A large amount of water glass is attached to the side of the columnar flask. Water glass is not attached to the inner surface of the cylindrical flask.

A white substance that has been produced by a reaction with the carboxyl group is attached to the formed object.

d) In a case where the amount of carboxyl group is 0.0100 mol/kg

Water glass is attached to the side of the columnar flask.

Water glass is not attached to the inner surface of the cylindrical flask.

e) In a case where the amount of carboxyl group is 0.0010 mol/kg

Water glass is attached to the side of the columnar flask.

Water glass is not attached to the inner surface of the cylindrical flask.

f) In a case where the amount of carboxyl group is 0.0001 mol/kg

Sand is attached to the side of the columnar flask.

Water glass is attached to the inner surface of the cylindrical flask.

The experimental results are summarized in Table 2.

TABLE 2

| Example/ Comparative Example | Material No. | Material type Functional group | Amount of carboxyl group [mol/kg] | Attachment to side of columnar flask | Evaluation Fixing to inner surface of cylindrical flask | Formed object (release properties) |
|---|---|---|---|---|---|---|
| Example | Material 12 | Carboxyl group | 0.1500 | Attached (dirt) * | None | Attached reactant (large amount) |
| Example | Material 13 | Carboxyl group | 0.1000 | Attached (dirt) * | None | Attached reactant (large amount) |
| Example | Material 14 | Carboxyl group | 0.0500 | Attached (water glass) | None | Attached reactant (large amount) |
| Example | Material 15 | Carboxyl group | 0.0100 | Attached (water glass) | None | Attached reactant (small amount) |
| Example | Material 16 | Carboxyl group | 0.0010 | Attached (water glass) | None | Attached reactant (small amount) |
| Example | Material 17 | Carboxyl group | 0.0001 | Attached (sand) * | Present * | Release failure * |

* represents that the material has a problem

Based on the experimental results, the following evaluation results are obtained.

I) For the amount of carboxyl group of 0.0001 mol/kg or less, sand in the material for the formed object is attached to the columnar flask, water glass is attached (fixed) to the cylindrical flask, and an effect of the reaction (release properties) is not obtained. From this, the amount of carboxyl group is assumed to be insufficient.

II) For the amount of carboxyl group of more than 0.0001 mol/kg and 0.0500 mol/kg or less, water glass is not attached (fixed) to the inner surface of the cylindrical flask. Attachment of water glass to the columnar flask is caused by an increase in the amount of water glass. This increase is for markedly exhibiting attachment difference (test results). The effect of the reaction of the formed object (release properties) is good, and the amount of carboxyl group is preferred.

III) For the amount of carboxyl group of more than 0.0100 mol/kg, a substance derived from thermal properties other than the carboxyl group accumulates, and the effect of thermal degradation is remarkable. Another factor needs to be confirmed to use the carboxyl group as a preferable mold release agent, although the carboxyl group reacts with the water glass component.

IV) According to I) to III), it was verified that the suitable amount of carboxyl group was more than 0.0001 mol/kg and 0.0500 mol/kg or less. Specifically, a result is obtained in which a mold release agent for forming a water glass-containing sand mold containing an organic compound having the amount of carboxyl group described above can be provided as the mold release agent for forming a water glass-containing sand mold that can solve the problem.

As described above, the embodiments of the present invention can provide a high-performance mold release agent for forming a water glass-containing sand mold, which has high release properties, so that attachment (fixing) of water glass to the flask and accumulation of water glass on the flask are prevented when forming the sand mold (main mold and core) using water glass as a binder.

The invention claimed is:

1. A mold release agent for forming a water glass-containing sand mold, the mold release agent being applied to an inner surface of a flask and raw material forming the water glass-containing sand mold being introduced into the flask,
    wherein the mold release agent contains an organic compound having a proton-donating functional group,
    wherein the proton-donating functional group is allowed to react with the water glass contained in the raw material of the sand mold, and
    the reaction performed between the proton-donating functional group and the water glass produces silicon dioxide preventing fixation between the sand mold containing the water glass therein and the inner surface of the flask.

2. The mold release agent for forming a water glass-containing sand mold according to claim 1, wherein the organic compound includes the proton-donating functional group selected from the group consisting of a carboxyl group, a carbonyl group and a hydroxyl group.

3. The mold release agent for forming a water glass-containing sand mold according to claim 2, wherein the organic compound is a chain organic compound having a carboxyl group in an amount of more than 0.0001 mol/kg and 0.0500 mol/kg or less.

* * * * *